United States Patent
Kennedy et al.

(10) Patent No.: US 6,722,202 B1
(45) Date of Patent: Apr. 20, 2004

(54) METHOD AND APPARATUS FOR INSPECTING A STRUCTURE UTILIZING MAGNETICALLY ATTRACTED PROBES

(75) Inventors: James C. Kennedy, Renton, WA (US); Christopher L. Mares, Orting, WA (US); Mark A. Negley, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 10/620,464

(22) Filed: Jul. 16, 2003

(51) Int. Cl.⁷ ................................................. G01N 9/24
(52) U.S. Cl. ........................... 73/634; 73/639; 73/643; 73/644
(58) Field of Search .................... 73/634, 635, 639, 73/640, 641, 643, 644

(56) References Cited

U.S. PATENT DOCUMENTS

| | | | |
|---|---|---|---|
| 4,149,419 A | * 4/1979 | Connell, Jr. et al. | .......... 73/621 |
| 4,235,112 A | * 11/1980 | Kaiser | .......... 73/634 |
| 4,479,388 A | * 10/1984 | Matzuk | .......... 73/634 |
| 5,161,413 A | * 11/1992 | Junker et al. | .......... 73/634 |
| 5,313,950 A | * 5/1994 | Ishikawa et al. | .......... 600/462 |
| 5,353,354 A | * 10/1994 | Keller et al. | .......... 382/128 |
| 5,398,691 A | 3/1995 | Martin et al. | |
| 5,505,204 A | * 4/1996 | Picot et al. | .......... 600/507 |
| 5,915,277 A | * 6/1999 | Patton | .......... 73/601 |
| 6,122,538 A | * 9/2000 | Sliwa, Jr. et al. | .......... 600/407 |

* cited by examiner

*Primary Examiner*—Hezron Williams
*Assistant Examiner*—Jacques M. Saint-Surin
(74) *Attorney, Agent, or Firm*—Alston & Bird LLP

(57) ABSTRACT

An apparatus and method for inspecting a structure are provided in which probes including respective sensing elements, such as ultrasonic transducers, are disposed proximate the opposed surfaces of a structure, but only one of the probes need be driven. In this regard, a tracking probe may be magnetically coupled to a driven probe and move in coordination therewith. The apparatus and method can therefore inspect structures in which one surface is inaccessible. The probes may permit liquid to be bubbled between the ultrasonic transducer and the structure in order to couple the ultrasonic signals. By utilizing a bubbled liquid as a couplant, the apparatus and method may operate in an ultrasonic array mode. Additionally, the probes may include at least one contact member, such as a plurality of wheels, for contacting the structure in order to maintain the desired orientation and spacing of the probes relative to the structure.

33 Claims, 2 Drawing Sheets

Figure 1:
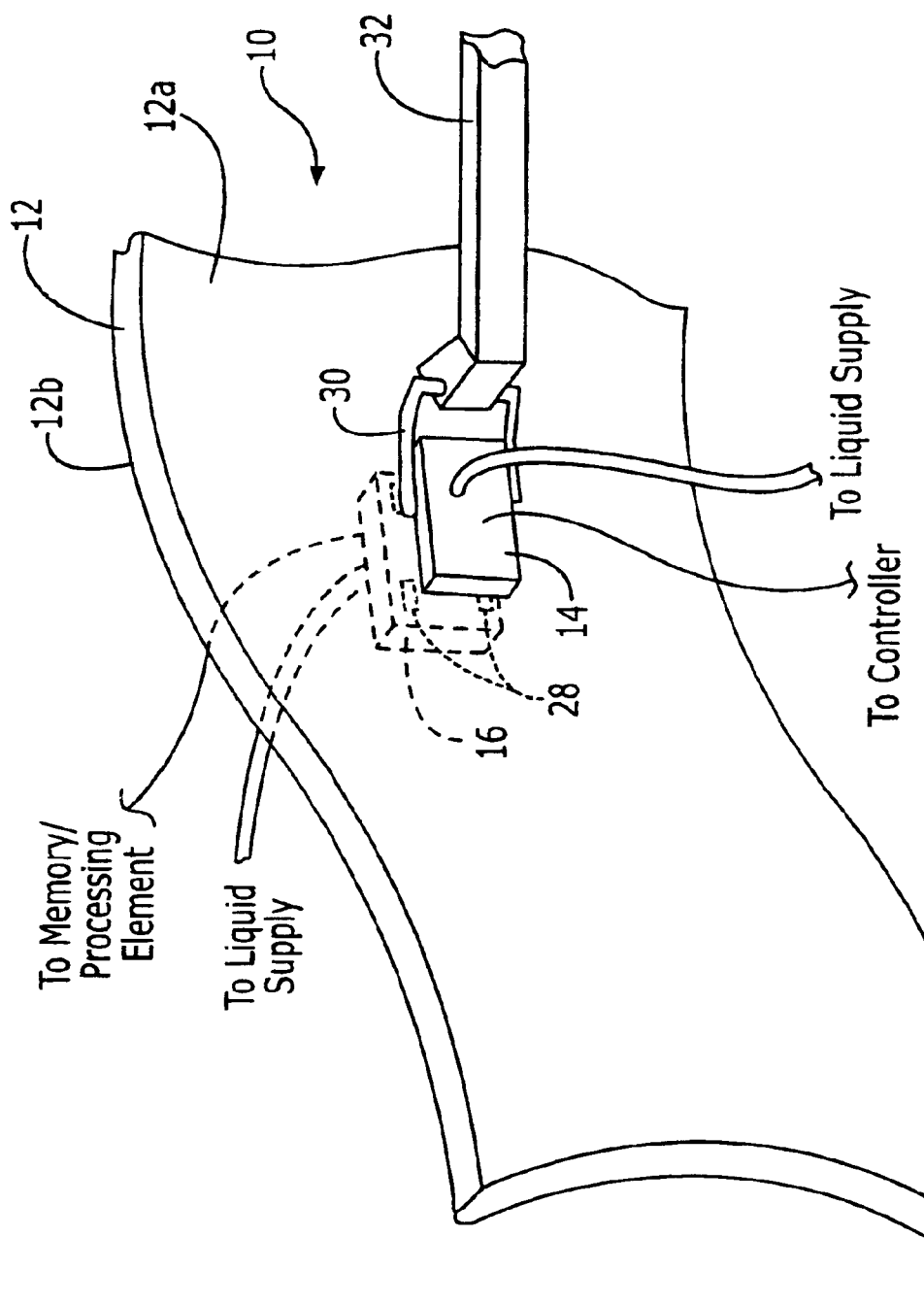

METHOD AND APPARATUS FOR INSPECTING A STRUCTURE UTILIZING MAGNETICALLY ATTRACTED PROBES

FIELD OF THE INVENTION

The present invention relates generally to an apparatus and method for inspecting a structure and, more particularly, to an apparatus and method for inspecting a structure that utilizes a driven probe proximate one surface of the structure and a tracking probe proximate the opposed surface of the structure with the driven and tracking probes being magnetically attracted to one another through the structure such that the tracking probe moves in concert with the driven probe as the driven probe is advanced over the structure.

BACKGROUND OF THE INVENTION

Non-destructive inspection of structures involves thoroughly examining a structure without harming the structure or requiring significant disassembly of the structure. Non-destructive inspection is advantageous for many applications in which a thorough inspection of the exterior and/or interior of a structure is required. For example, non-destructive inspection is commonly utilized in the aircraft industry to inspect aircraft structures for any type of internal or external damage to the structure.

Among the structures that are routinely non-destructively tested are composite structures. In this regard, composite structures are commonly used throughout industry because of their engineering qualities, design flexibility and low weight. As such, it is frequently desirable to inspect composite structures to identify any flaws, such as cracks, voids or porosity, which could adversely affect the performance of the composite structure.

Various types of sensors may be utilized to perform non-destructive inspection. One or more sensors may move over the portion of the structure to be examined, and receive data regarding the structure. For example, a pulse-echo, thru-transmission, or shear wave sensor may be utilized to obtain ultrasonic data, such as thickness gauging, detection of laminar defects and porosity, and/or crack detection in the structure. Resonance, pulse echo or mechanical impedance sensors may be utilized to provide indications of voids or porosity, such as in adhesive bondlines of the structure. The data acquired by the sensors is typically processed by a processing, element, and the processed data may be presented to a user via a display.

The non-destructive inspection may be performed manually by technicians who typically move an appropriate sensor over the structure. The manual scanning generally consists of a trained technician holding a sensor and moving the sensor along the structure to ensure the sensor is capable of testing all desired portions of the structure. In many situations, the technician must repeatedly move the sensor side-to-side in one direction while simultaneously indexing the sensor in another direction. For a technician standing beside a structure, the technician may repeatedly move the sensor right and left, and back again, while indexing the sensor between each pass. In addition, because the sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data. Thus, manual scanning-of structures is time-consuming, labor-intensive, and prone to human error.

Automated inspection systems have been developed to overcome the myriad of shortcomings with manual inspection techniques, but the automated systems may sometimes be too expensive, too bulky and/or require access to portions of a structure that are difficult, if not impossible, to access. For example, the AUSS system is a complex mechanical scanning system that employs through-transmission ultrasonic inspection. The AUSS system can also perform pulse echo inspections, and simultaneous dual frequency inspections. The AUSS system has robotically conrtrolled probe arms that must be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. As will be apparent, conventional automated scanning systems, such as the AUSS system, therefore require access to both sides or surfaces of a structure which, at least in some circumstances, will be problematic, if not impossible. In order to maintain the ultrasonic transmitter and receiver in proper alignment and spacing with one another and with the structure undergoing inspection, the AUSS system has a complex positioning system that provides motion control in ten axes. As will be recognized, this requirement that the orientation and spacing of the ultrasonic transmitter and receiver be invariant with respect to one another and with respect to the structure undergoing inspection is especially difficult in conjunction with the inspection of curved structures.

In order to increase the rate or speed at which the inspection of a structure is conducted, the scanning system may include ultrasonic probes that have arrays of ultrasonic transmitters and receivers. As such, the inspection of the structure can proceed more rapidly and efficiently, thereby reducing the costs associated with the inspection. Unfortunately, the use of arrays of ultrasonic transmitters and receivers is generally impractical during the scanning of curved structures, such as large-scale curved composite structures. In this regard, conventional ultrasonic scanning systems for inspecting large-scale curved composite parts utilize water jets to provide water between the surface of the structure undergoing inspection and the ultrasonic transmitter or receiver in order to effectively couple ultrasonic signals into and out of the structure. In instances in which the ultrasonic probes include an array of ultrasonic transmitters or receivers, it has been difficult to design a corresponding water jet array that does not produce significant interference or crosstalk between the elements of the array.

BRIEF SUMMARY OF THE INVENTION

In light of the foregoing background, an improved apparatus and method for inspecting a structure, such as a composite structure and, in particular, a curved composite structure, are provided according to the various embodiments of the present invention. Although the method and apparatus of the present invention utilize probes including respective sensing elements, such as respective ultrasonic transducers, that are disposed proximate the opposed surfaces of a structure, only one of the probes need be driven, such as by means of a robotic arm or the like. Thus, the method and apparatus of the present invention are advantageously adapted to inspect structures in which a surface of the structure is relatively inaccessible, at least for a robotic arm or the like. Additionally, embodiments of the method and apparatus of the present invention are capable of operating in an ultrasonic array mode, even in conjunction with the inspection of curved structures, thereby increasing the speed and efficiency with which such structures may be inspected and correspondingly reducing the cost associated with the inspection. Further, embodiments of the method and apparatus of the present invention permit the probes to contact and ride along the respective surfaces of the structure, thereby reducing the necessary sophistication of the motion control system that is otherwise required by conventional scanning systems in order to maintain the ultrasonic probes in a predefined orientation and at a predefined spacing from the respective surface of a structure undergoing inspection.

The apparatus of the present invention includes a driven probe disposed proximate a first surface of the structure and a tracking probe disposed proximate an opposed second surface of the structure. The driven probe is moved along the first surface of the structure in response to the application of motive force, such as by means of a robotic arm or other positioning system. In contrast, the tracking probe generally moves along the second surface of the structure in response to the movement of the driven probe and independent of the application of any other motive force. Thus, the tracking probe generally passively follows the movement of the driven probe such that the tracking probe need not be engaged by a robotic arm or other positioning system. The tracking probe can therefore be disposed on the backside or other surface of a structure that is relatively inaccessible.

To facilitate the coordinated movement of the tracking probe in conjunction with the driven probe, both the driven probe and the tracking probe advantageously include a magnet which draws the driven and tracking probes toward the first and second surfaces of the structure, respectively. Additionally, the magnetic attraction between the magnets of the driven and tracking probes causes the tracking probe to be moved over the second surface of the structure in response to corresponding movement of the driven probe.

The driven probe includes a sensing element for inspecting a structure as the driven probe is moved along the first surface of the structure. While the sensing element may be an x-ray detector, a camera or the like, the sensing element is typically an ultrasonic transducer. Typically, the tracking probe also includes a sensing element, such as an ultrasonic transducer. The ultrasonic transducers may be an ultrasonic transmitter, an ultrasonic receiver, or both.

In order to facilitate the coupling of the ultrasonic signal between the ultrasonic transducer of the driven probe and the structure, a couplant may be disposed between the ultrasonic transducers and the respective surfaces of the structure. While air or water jets may be utilized a couplant, the driven probe of one advantageous embodiment may also include an inlet for liquid that is bubbled between the ultrasonic transducer and the first surface of the structure. In this regard, the driven probe may include a housing in which the magnet and the ultrasonic transducer are disposed, and which defines the inlet. The inlet may be in fluid communication with that portion of the ultrasonic transducer that faces the first surface of the structure. Thus, the liquid bubbled between the ultrasonic transducer and the first surface of the structure facilitates coupling of the ultrasonic signals produced by the ultrasonic transducer into the structure. Likewise, the tracking probe may include an inlet for liquid that is bubbled between the ultrasonic transducer of the tracking probe and the second surface of the structure. In this regard, the tracking probe can also include a housing in which the magnet and the ultrasonic transducer are disposed, and which defines the inlet. Again, the inlet is in fluid communication with that portion of the ultrasonic transducer of the tracking probe that faces the second surface of the structure. Thus, ultrasonic signals emerging from the structure can be effectively coupled to the ultrasonic transducer of the tracking probe by the liquid bubbled therebetween. By bubbling liquid between the ultrasonic transducers and the respective surfaces of the structure, water jets are not required such that the ultrasonic transducers of the driven and tracking probes may include arrays of ultrasonic transducers, thereby permitting the rate at which the structure is inspected to be increased and the associated inspection cost accordingly decreased.

According to one advantageous embodiment, the driven probe includes at least one contact member, such as a plurality of wheels, for contacting the first surface of the structure. Thus, the driven probe may ride along the first surface of the structure. As such, the orientation of the driven probe relative to the first surface of the structure and the spacing of the driven probe relative to the first surface of the structure may be maintained by the contact between the driven probe and the first surface of the structure without requiring the complex motion control systems utilized by conventional scanning systems. Likewise, the tracking probe may include at least one contact member, such as a plurality of wheels, for contacting the second surface of the structure such that the tracking probe is also capable of riding therealong. Like the driven probe, the tracking probe may therefore be maintained in a predefined orientation and at a predefined spacing relative to the second surface of the structure without requiring the complex motion control systems utilized by conventional scanning systems. This independence from the motion control systems utilized by conventional scanning systems further reduces the cost of the apparatus of the present invention and permits the tracking probe to be moved in a controlled fashion over a surface of a structure that is relatively inaccessible for a robotic arm or other conventional motion control system. The driven and tracking probes may also utilize the water that is bubbled over the surface of the structure as a water bearing to maintain their spacing and orientation.

According to another aspect of the present invention, a method of inspecting a structure is provided. In this regard, the driven probe is positioned proximate the first surface of the structure, and the tracking probe is positioned proximate the opposed second surface of the structure. For example, driven and tracking probes may be disposed in contact with the first and second surfaces of the structure, respectively, thereby simplifying the alignment and spacing of the probes relative to the respective surfaces of the structure. The method of inspecting a structure also establishes magnetic attraction between the driven and tracking probes such that the driven and tracking probes are drawn toward the first and second surfaces of the structure, respectively. The driven probe is then moved along the first surface of the structure, such as in response to the application of a motive force by a robotic arm or other positioning system. The movement of the driven probe and the magnetic attraction between the driven and tracking probes causes the tracking probe to be correspondingly moved along the second surface of the structure. Advantageously, the tracking probe moves along the second surface of the structure independent of the application of any motive force. Thus, the tracking probe may be disposed proximate a relatively inaccessible surface of a structure since the movement of the tracking probe need not be controlled by a robotic arm or other positioning system.

As the driven probe is moved along the first surface of the structure, ultrasonic signals are transmitted to the structure by the ultrasonic transducer of one of the probes and are received by the ultrasonic transducer of the other probe following propagation through the structure. In order to effectively couple the ultrasonic signals between the driven and tracking probes and the structure, a liquid may be bubbled between the driven and tracking probes and the first and second surfaces of the structure, respectively, while ultrasonic signals are transmitted into and received from the structure. By coupling the ultrasonic signals by means of a bubbled liquid, the driven and tracking probes may include respective arrays of ultrasonic transducers in order to increase the speed with which the structure is inspected and to correspondingly decrease the cost of inspection. Alternatively, air or water jets may be utilized as the couplant.

BRIEF DESCRIPTION OF THE SEVERAL VIEWS OF THE DRAWING(S)

Figure 2A:
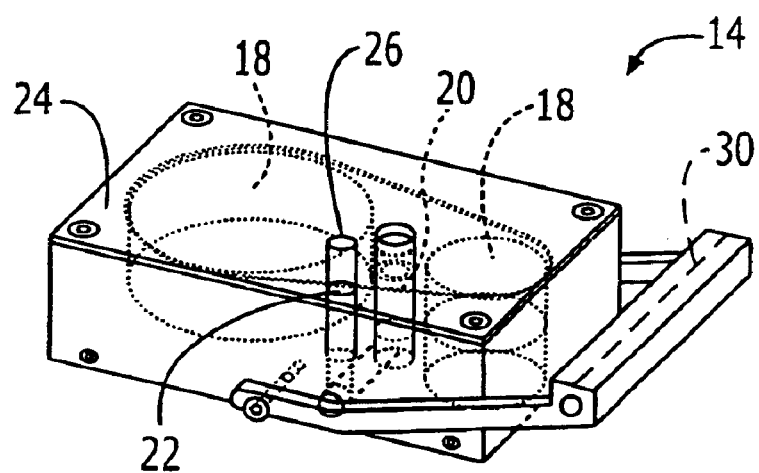
Figure 2B:
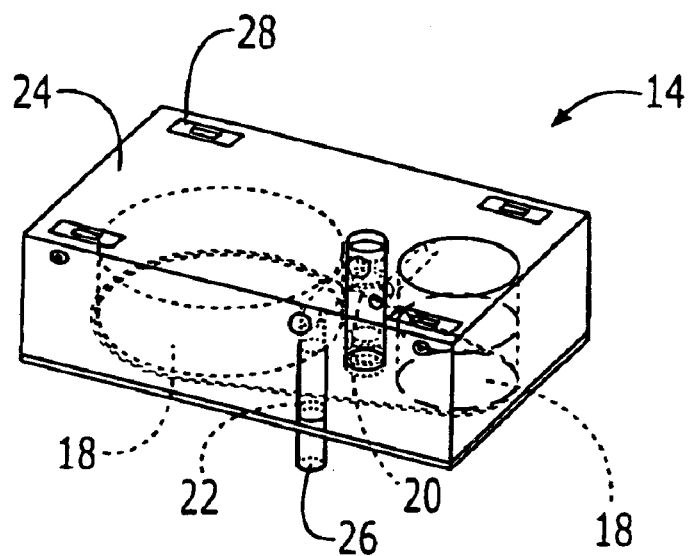

Having thus described the invention in general terms, reference will now be made to the accompanying drawings, which are not necessarily drawn to scale, and wherein:

FIG. 1 is a perspective view of an apparatus according one embodiment of the present invention in which driven and tracking probes are disposed proximate the opposed surfaces of a structure; and FIGS. 2a and 2b are schematic perspective views of a driven probe of an apparatus according to one embodiment of the present invention in which various components of the driven probe that are disposed within the housing are illustrated by dashed lines.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Referring now to FIG. 1, an apparatus 10 for inspecting a structure 12 according to one embodiment of the present invention is depicted. The apparatus can inspect a variety of structures formed of various materials. Since the apparatus relies to some extent upon the establishment of magnetic fields through the structure, however, the structure is preferably non-magnetic, that is, the structure preferably has no magnetic permeability. For example, the structure may be a composite structure, such as a honeycomb composite structure. While a portion of a relatively simple structural panel is depicted during the course of an inspection in FIG. 1, the structure may have a myriad of shapes and sizes. In addition, the structure that is inspected may be utilized in a wide variety of applications, including in vehicular applications, such as in conjunction with aircraft, marine vehicles, automobiles, space craft and the like, as well as other non-vehicular applications, such as in conjunction with buildings and other construction projects. Moreover, the structure may be inspected prior to assembly or following assembly, as desired.

The apparatus 10 of the present invention includes a driven probe 14 disposed proximate a first surface 12a of the structure 12 and a tracking probe 16 disposed proximate an opposed second surface 12b of the structure. As described below, the driven and tracking probe may be disposed in contact with the first and second surfaces of the structure, respectively. The driven and tracking probes are advantageously initially positioned so as to be directly opposed one another or otherwise in positional correspondence with one another, as shown in FIG. 1. As described below, this positional relationship or correspondence between the driven and tracking probes is maintained as the probes are moved along the respective surfaces of the structure.

Each probe 14, 16 includes at least one magnet 18. In this regard, FIGS. 2a and 2b depict a driven probe having a pair of magnets. Although not depicted, the tracking probe could similarly have a pair of magnets. While various types of magnets may be utilized, the driven and tracking probes of one embodiment include permanent magnets, such as NdFeB magnets. As explained hereafter, the magnets of the driven and tracking probes magnetically attract the driven and tracking probes toward the respective surfaces of the structure 12. Thus, the number and size of magnets for both the driven and tracking probes will be dependent, at least in part, upon the weight of the respective probes, the thickness of the structure undergoing inspection and the material that forms the structure undergoing inspection. Additionally, while the driven probe of FIGS. 2a and 2b includes a pair of magnets of dissimilar size, the driven probe may include only a single magnet or multiple magnets having either the same or different sizes. Likewise, the tracking probe may include the same number and sizes of magnets as the driven probe, or a different number and/or size of magnet so long as sufficient magnetic attraction between the driven and tracking probes is provided.

For probes 14, 16 that include an array of magnets 18, the spacing between the magnets of the array is preferably greater than the spacing between the driven and tracking probes. As such, this relationship provides a stable position of alignment between the probes. The alignment of the probes could be further enhanced by selecting the magnetic polarity of one magnet of one of the probes to be such that the respective magnet is repelled by the magnets of the other probe. However, the other probe may include a plug of ferromagnetic material that is aligned with the respective magnet having the opposite polarity. Since the ferromagnetic plug does not repel the magnet of the opposite polarity, the probes would be attracted to one another when these elements are properly aligned. If the probes were misaligned, however, the probes would be repelled. As such, the magnet of opposite polarity and the corresponding ferromagnetic plug serve as a magnetic key to aid in the alignment of the probes.

In determining the number and type of magnets 18 to be included in the probe 14, 16, the weight of the magnets, the surface area of the magnets and the increased demagnetization effects attributable to the length to diameter ratio of the magnet are generally taken into account. In this regard, magnets that are relatively thin and flat may have a substantial surface area so as to generate significant magnetic flux. However, these magnets are generally inefficient since they suffer from increased demagnetization effects due to their relatively small length to diameter ratio relative to more rod-like magnets having a smaller surface area At least one of the probes 14, 16, such as the driven probe, includes a sensing element 20 for inspecting the structure 12 as the probe is moved over the respective surface of the structure. The probe may include a variety of sensing elements, such as a camera, an x-ray detector, such as a relatively small solid-state x-ray linear detector, or the like. In one advantageous embodiment, however, the sensing element is an ultrasonic transducer, such an ultrasonic transmitter and/or an ultrasonic receiver, for ultrasonically inspecting the structure as the probe is moved over the respective surface of the structure. For example, the ultrasonic transducer may be a 1 MHz immersion transducer from Agfa/Krautkramer of Lewistown, Pa. In this regard, certain embodiments of the present invention provide for the inspection of the structure by means of a through transmission technique. In these embodiments, both, the driven and tracking probes include a respective sensing element, such as a respective ultrasonic transducer such that ultrasonic signals can be transmitted into the structure from the ultrasonic transducer of one-probe, such as the driven probe, and thereafter received by the ultrasonic transducer of the other probe, such the tracking probe, following transmission through the structure. By analyzing the ultrasonic signals following transmission through the structure, various flaws within the structure, such as cracks, voids and/or porosity, may be identified as known to those skilled in the art.

Although not described in detail hereinafter, both the driven and tracking probes 14, 16 of the apparatus 10 of other embodiments need not include a sensing element 20. In these other embodiments, for example, only one of the probes need include a sensing element with the inspection being conducted from one side of the structure 12. For example, one of the probes may include an ultrasonic transducer that is operated in a reflection or pulse echo mode. Thus, the same ultrasonic transducer both transmits and receives ultrasonic signals in this exemplary alternative embodiment. As another alternative example, the sensing element may be a camera that captures images of the respective surface of the structure from one side thereof In these alternative embodiments, therefore, the probe that does not include a sensing element effectively serves to magnetically attract the probe with the sensing element to the respective surface of the structure. In the embodiments described hereinafter, however, both the driven and tracking probes include a respective sensing element, such as an ultrasonic transducer.

In order to facilitate the coupling of ultrasonic signals between the ultrasonic transducer(s) 20 of the driven and/or tracking probes 14, 16 and the structure 12, a couplant may be utilized. While air or water jets may be utilized as a couplant, the driven and/or tracking probes may include an inlet 22 for a liquid, such as water, that is bubbled between the ultrasonic transducer and a respective surface 12a, 12b of the structure. As shown in FIGS. 2a and 2b in conjunction with the driven probe of one embodiment of the present invention, the driven probe also includes a housing 24 in which the magnets 18 and the sensing element, such as the ultrasonic transducer, are disposed. The housing may be constructed of various non-magnetic materials and, in one embodiment, is constructed of Lucite® material available from E.I. DuPont Nemours and Company of Wilmington, Del.

As shown in FIGS. 2a and 2b in conjunction with the driven probe 14 of one embodiment of the present invention, the housing 24 defines the inlet 22 which, in turn, is in fluid communication with that portion of the ultrasonic transducer 20 that faces the first surface 12a of the structure 12. In this regard, the ultrasonic transducer is positioned within the housing such that the portion of the ultrasonic transducer that, faces the first surface of the structure is spaced somewhat, i.e., is recessed, from the surface of the housing that faces the structure. Thus, liquid that is introduced through the inlet flows through an internal channel defined by the housing and effectively fins the gap between the ultrasonic transducer and the first surface of the structure. Advantageously, the liquid flows smoothly over the ultrasonic transducer with no bubbles, cavitation or turbulence that could otherwise detrimentally affect the signal to noise ratio.

Although not shown in FIGS. 2a and 2b, a source of liquid is connected to the inlet 22 defined by the housing 24. To facilitate this connection, a tube 26, such as a brass tube or the like, may be connected to the housing and extend outwardly therefrom. While the tube maybe connected to the housing in various manners, the tube may engage the housing by means of an interference or press fit of the tube into the inlet defined by the housing. Although not separately depicted, those embodiments of the tracking probe 16 that also include an ultrasonic transducer 20 preferably similarly have an inlet through which liquid, such as water, is introduced such that the liquid may be bubbled between the ultrasonic transducer and the second surface 12b of the structure 12, as described above in conjunction with the driven probe 14.

In operation, the driven and tracking probes 14, 16 are disposed proximate the first and second surfaces 12a, 12b of the structure. 12. As shown in FIG. 1, the driven and tracking probes may advantageously be disposed in contact with the respective surfaces of the structure. In order to facilitate the contact of the probes with the respective surfaces of the structure and to avoid any undesirable damage or other marring of the respective surfaces of the structure as the result of contact with the probes, the driven and tracking probes can each also include at least one contact member 28. Typically, the contact member(s) extend outwardly from the surface of the housing 24 that faces the respective surface of the substrate. Various types of contact members can be utilized, such as skids or the like. In one embodiment, however, the driven and tracking probes each include a plurality of wheels that contact the respective surface of the structure and that permit the probe to ride therealong.

By permitting contact between the driven and tracking probes 12, 16 and the respective surfaces 12a, 12b of the structure 12, the orientation of the probes and, more particularly, the sensing elements, such as the ultrasonic transducers, of the probes may be maintained without requiring the orientation of the probes to be controlled by means of a complex motion control system or other type of positioning system. Additionally, the contact between the driven and tracking probes and the respective surfaces of the structure maintains a consistent spacing between the respective sensing elements, such as the respective ultrasonic transducers, and the structure, similarly without requiring complex motion control systems or other positioning systems. While a contact member, such as wheels, is advantageous, the probes may utilize the water that serves as a couplant as a water bearing to maintain the spacing and orientation of the probes.

The operation of the apparatus 10 of the present invention will now be described in conjunction with driven and tracking probes 14, 16 configured to conduct a through transmission ultrasonic inspection. However, the driven and tracking probes may be utilized in other manners as described below. By way of example of the operation of one embodiment of the driven and tracking probes, however, the driven and tracking probes are disposed proximate to and generally in contact with the opposed first and second surfaces 12a, 12b of a structure 12 while maintaining alignment and magnetic attraction between the probes.

Liquid, such as water, is then bubbled through the inlet 22 of each probe and between the ultrasonic transducers 20 and the respective surfaces 12a, 12b of the substrate 12. Additionally, the ultrasonic transducers are activated such that ultrasonic transducer of one probe, such as the driven probe 14, emits ultrasonic signals into the structure. Although not shown, a drive element, such as a voltage or current source, is generally associated with the ultrasonic transducer of the driven probe so as to actuate the ultrasonic transducer to emit the ultrasonic signals. This drive element may be co-located with the driven probe or may be remote therefrom and electrically connected to the ultrasonic transducer. Correspondingly, the ultrasonic transducer of the other probe, such as a tracking probe 16, receives the ultrasonic signals originally transmitted by the ultrasonic transducer of the driven probe following the propagation of the ultrasonic signals through the structure.

While the ultrasonic signals are transmitted through the structure 12 and liquid is bubbled over the respective ultrasonic transducers 20, the driven probe 14 is moved along the first surface 12a of the structure. While the motive force required to move the driven probe along the first surface of the structure may be applied in various manners, the driven probe of the illustrated embodiment includes a handle 30 that is engaged by a robotic arm 32 as shown in FIG. 1 or the like. As known to those skilled in the art, the robotic arm can be controlled by a motion control system or other positioning system so as to controllably move the driven probe in a predefined manner and in accordance with a defined pattern along the first surface of the structure. Since the driven-probe is in contact with and rides along the first surface of the structure, the motion control system or other positioning system need not be as complex as that required by conventional scanning systems. By way of comparison to the AUSS system that requires a motion control system capable of controllably positioning the probes about ten axes, the motion control system utilized in conjunction with the apparatus 10 of one embodiment of the present invention need only controllably position the probes in half the number of axes.

As a result of the magnetic attraction established between the driven and tracking probes 14, 16 and, more particularly, between the magnets 18 of the driven and tracking probes, the tracking probe moves in a like manner and in correspondence with the driven probe without requiring the application of any additional motive force directly to the tracking probe. Thus, the tracking probe moves so as to remain in an aligned, opposed position relative to the driven probe as the driven probe is moved along the first surface 12a of the structure 12. As such, the tracking probe need not be engaged by a robotic arm or other positioning system. Accordingly, the tracking probe can be disposed proximate to and can ride along a second surface 12b of a structure that is relatively inaccessible, such as the interior of a cylindrical structure or other structure having a closed shape.

The ultrasonic signals that are received by the ultrasonic transducer 20 of the tracking probe 16 can be stored along with an indication of the time at which the ultrasonic signals are received and/or an indication of the relative position of the tracking probe when the ultrasonic signals are received. The ultrasonic signals may be stored by a memory device that is either co-located with the tracking probe or remote from the tracking probe and electrically connected therewith. By analyzing, the ultrasonic signals received by the ultrasonic transducer of the tracking probe, the integrity of the structure 12 as well as any flaws therein can be determined in the manner known to those skilled in the art.

By bubbling liquid between the ultrasonic transducer 20 and the respective surface of the structure 12, the ultrasonic signals are effectively coupled into and out of the structure in one advantageous embodiment. Moreover, while a single ultrasonic transducer is depicted in FIGS. 2a and 2b, the driven and/or tracking probes 14, 16 may include an array of ultrasonic transducers since the coupling provided by the bubbled liquid permits inspection in an ultrasonic array mode, thereby increasing the speed with which the inspection is performed and correspondingly reducing the cost associated with the inspection.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for ultrasonically inspecting a structure comprising:
    a driven probe disposed proximate a first surface of the structure, said driven probe comprising a magnet and an ultrasonic transducer for inspecting the structure as said driven probe is moved over the first surface of the structure; and
    a tracking probe disposed proximate an opposed second surface of the structure, said tracking probe also comprising a magnet for cooperating with the magnet of said driven probe to draw the driven and tracking probes toward the first and second surfaces of the structure, respectively, wherein magnetic attraction between said driven and tracking probes causes said tracking probe to be moved over the second surface of the structure in response to corresponding movement of said driven probe.

2. An apparatus according to claim 1 wherein said driven probe further comprises an inlet for liquid that is bubbled between the ultrasonic transducer and the first surface of the structure.

3. An apparatus according to claim 2 wherein said driven probe further comprises a housing in which the magnet and the ultrasonic transducer are disposed and which defines the inlet, and wherein the inlet is in communication with that portion of the ultrasonic transducer that faces the first surface of the structure.

4. An apparatus according to claim 2 wherein the liquid bubbled between the ultrasonic transducer and the first surface of the structure serves as a water bearing.

5. An apparatus according to claim 1 wherein said tracking probe further comprises an ultrasonic transducer for communicating with the ultrasonic transducer of said driven probe.

6. An apparatus according to claim 5 wherein said tracking probe further comprises an inlet for liquid that is bubbled between the ultrasonic transducer and the second surface of the structure.

7. An apparatus according to claim 6 wherein said tracking probe further comprises a housing in which the magnet and the ultrasonic transducer are disposed and which defines the inlet, and wherein the inlet is in communication with that portion of the ultrasonic transducer that faces the second surface of the structure.

8. An apparatus according to claim 6 wherein the liquid bubbled between the ultrasonic transducer and the second surface of the structure serves as a water bearing.

9. An apparatus according to claim 1 wherein said driven probe comprises at least one contact member for contacting the first surface of the structure such that said driven probe is capable of riding therealong.

10. An apparatus according to claim 9 wherein said at least one contact member comprises a plurality of wheels.

11. An apparatus according to claim 1 wherein said tracking probe comprises at least one contact member for contacting the second surface of the structure such that said tracking probe is capable of riding therealong.

12. An apparatus according to claim 11 wherein said at least one contact member comprises a plurality of wheels.

13. An apparatus according to claim 1 wherein the ultrasonic transducer of said driven probe comprises an array of ultrasonic transducers.

14. An apparatus according to claim 1 wherein said driven and tracking probes each comprises an array of magnets, and wherein at least one element of the array of each probe is different than the other elements to thereby serve as a magnetic key.

15. An apparatus for inspecting a structure comprising:
a driven probe disposed proximate a first surface of the structure, said driven probe comprising a magnet and at least one contact member for contacting the first surface of the structure such that said driven probe is capable of riding therealong; and
a tracking probe disposed proximate an opposed second surface of the structure, said tracking probe also comprising a magnet for cooperating with the magnet of said driven probe to draw the driven and tracking probes toward the first and second surfaces of the structure, respectively, wherein magnetic attraction between said driven and tracking probes causes said tracking probe to be moved over the second surface of the structure in response to corresponding movement of said driven probe, and
wherein at least one of said driven probe and said tracking probe further comprises a sensing element for inspecting the structure as said driven probe is moved over the first surface of the structure.

16. An apparatus according to claim 15 wherein the sensing element is selected from the group consisting of an x-ray detector and a camera.

17. An apparatus according to claim 15 wherein the sensing element comprises an ultrasonic transducer.

18. An apparatus according to claim 17 wherein said driven probe comprises the ultrasonic transducer and further comprises an inlet for liquid that is bubbled between the ultrasonic transducer and the first surface of the structure.

19. An apparatus according to claim 18 wherein said driven probe further comprises a housing in which the magnet and the ultrasonic transducer are disposed and which defines the inlet, and wherein the inlet is in communication with that portion of the ultrasonic transducer that faces the first surface of the structure.

20. An apparatus according to claim 17 wherein both said driven probe and said tracking probe comprise an ultrasonic transducer for communicating therebetween.

21. An apparatus according to claim 20 wherein said tracking probe further comprises an inlet for liquid that is bubbled between the ultrasonic transducer and the second surface of the structure.

22. An apparatus according to claim 21 wherein said tracking probe further comprises a housing in which the magnet and the ultrasonic transducer are disposed and which defines the inlet, and wherein the inlet is in communication with that portion of the ultrasonic transducer that faces the second surface of the structure.

23. An apparatus according to claim 21 wherein the liquid bubbled between the ultrasonic transducer and the second surface of the structure serves as a water bearing.

24. An apparatus according to claim 17 wherein the ultrasonic transducer comprises an array of ultrasonic transducers.

25. An apparatus according to claim 15 wherein said at least one contact member comprises a plurality of wheels.

26. An apparatus according to claim 15 wherein said tracking probe comprises at least one contact member for contacting the second surface of the structure such that said tracking probe is capable of riding therealong.

27. An apparatus according to claim 26 wherein said at least one contact member comprises a plurality of wheels.

28. An apparatus according to claim 15 wherein said driven and tracking probes each comprises an array of magnets, and wherein at least one element of the array of each probe is different than the other elements to thereby serve as a magnetic key.

29. A method of inspecting a structure comprising:
positioning a driven probe proximate a first surface of the structure and a tracking probe proximate an opposed second surface of the structure;
establishing magnetic attraction between the driven and tracking probes such that the driven and tracking probes are drawn toward the first and second surfaces of the structure, respectively;
moving the driven probe along the first surface of the structure which causes the tracking probe to be correspondingly moved along the second surface of the structure; and
transmitting ultrasonic signals into and receiving ultrasonic signals from the structure as the driven probe is moved along the first surface of the structure.

30. A method according to claim 29 wherein the driven probe moves along the first surface of the structure in response to the application of motive force, and wherein the tracking probe moves along the second surface of the structure in response to movement of the driven probe along the first surface of the structure and independent of the application of any other motive force.

31. A method according to claim 29 further comprising bubbling a liquid between the driven and tracking probes and the first and second surfaces of the structure, respectively, while ultrasonic signals are transmitted into and received from the structure.

32. A method according to claim 29 wherein positioning the driven and tracking probes proximate the first and second surfaces of the structure, respectively, comprises disposing the driven and tracking probes in contact with the first and second surfaces of the structure, respectively.

33. A method according to claim 29 wherein transmitting and receiving the ultrasonic signals comprises transmitting ultrasonic signals from one of the driven and tracking probes and receiving the ultrasonic signals after passing through the structure with the other of the driven and tracking probes.

* * * * *